United States Patent

Ramachandran

[11] Patent Number: 5,591,311
[45] Date of Patent: Jan. 7, 1997

[54] PROCESS FOR PURIFYING A 2,6-DIALKYLPHENOL

[75] Inventor: Venkataraman Ramachandran, Baton Rouge, La.

[73] Assignee: Albemarle Corporation, Richmond, Va.

[21] Appl. No.: 548,788

[22] Filed: Oct. 26, 1995

[51] Int. Cl.$^6$ .................... B01D 3/34; C07C 37/68
[52] U.S. Cl. ............... 203/36; 203/37; 203/95; 203/DIG. 16; 568/749; 568/756; 568/781
[58] Field of Search ............... 203/36, 37, 95, 203/DIG. 16; 568/781, 749, 756

[56] References Cited

U.S. PATENT DOCUMENTS

| | | | |
|---|---|---|---|
| 4,634,796 | 1/1987 | Suciu et al. | 568/757 |
| 5,091,058 | 2/1992 | Davie | 203/33 |
| 5,175,376 | 12/1992 | Nieminen et al. | 568/781 |
| 5,264,085 | 11/1993 | Inaba et al. | 203/39 |
| 5,487,816 | 1/1996 | Schulz et al. | 203/14 |

Primary Examiner—Nina Bhat
Attorney, Agent, or Firm—Philip M. Pippenger

[57] ABSTRACT

A process for purifying impure 2,6-diisopropylphenol (DIP) mixtures having lower and higher boiling phenolic impurities is described. The process involves washing the mixture with aqueous alkali metal hydroxide solution in an inert atmosphere and separating the aqueous and organic phases, washing the resulting organic phase with water, and then subjecting the water-washed organic phase to distillation in an inert environment to recover purified DIP. Since only one distillation is required rather than two, the development of impurities in the DIP caused by in situ oxidation reactions at elevated temperatures due to the inevitable presence of traces of air in commercial distillation facilities is reduced to acceptable levels.

27 Claims, No Drawings

PROCESS FOR PURIFYING A 2,6-DIALKYLPHENOL

TECHNICAL FIELD

This invention relates to a process for converting an impure 2,6-dialkylphenol, such as produced in a catalyzed phenol ortho-alkylation process, into a highly pure product. The invention is particularly well-adapted for the purification of 2,6-diisopropylphenol produced by catalytic ortho-alkylation of phenol with propylene.

BACKGROUND

Methods for the production of ortho-dialkylated phenols such as 2,6-diisopropylphenol are well-known and reported in the literature. The most efficacious process involves reacting phenol with an olefin such as propylene using an aluminum phenoxide catalyst, such as described in U.S. Pat. No. 2,831,898 to G. C. Ecke and A. J. Kolka. Modifications of this original phenol ortho-alkylation chemistry subsequently appeared, primarily involving catalyst alterations or modifications. In all such processes it is possible to achieve good selectivity in the production of the 2,6-dialkylphenol. Nevertheless the crude product mixtures typically contain impurities such as unreacted phenol, one or more monoalkylphenols, one or more dialkylphenol isomers other than the desired 2,6-dialkylphenol isomer, 2,4,6-trialkylphenol and phenolic ethers.

Recently, substantial commercial requirements for highly pure 2,6-diisopropylphenol (99.8% or more) have arisen. To fulfill these requirements on an economical basis, a concomitant need has arisen for technology enabling economical, large scale purification of crude phenol ortho-alkylation reaction product mixtures.

Production of high purity (99.8% and above) 2,6-diisopropylphenol by distillation is an extremely difficult operation—much more difficult than might first appear. A complicating factor is that other impurities are readily generated by oxidation reactions which occur at the elevated temperatures required during the distillation. These impurities include 2,6-diisopropylbenzoquinone, 2-isopropyl-6-isopropenylphenol, 2,6-diisopropenylphenol and 2,2-dimethyl-4-isopropyl-1,3-benzodioxole.

Laboratory studies have indicated that the formation of these impurities can be prevented if oxygen is totally excluded from the system. This, however, is not practical in most industrial distillation facilities carried out under vacuum, due to seepage of air through standard pipe flanges and fittings.

The formation of these and other impurities can be minimized by use of continuous rather than batch distillation, because the residence time—i.e., the time the material is held at the elevated temperatures—is much less in a continuous distillation. However in a situation of this kind, traditional continuous distillation alone requires two distillation columns to accomplish this separation, whereas batch distillation requires only a single column. Because of the considerable capital investment required for distillation columns, a batch distillation would be much preferred were it not for the longer durations of exposure of the material to high temperatures and the practical difficulty of rigorously excluding air in such operations when conducted on a large scale.

U.S. Pat. No. 5,175,376 to K. M. Niemenen and P. K. Essen describes a purification procedure for 2,6-diisopropylphenol which involves subjecting the impure 2,6-diisopropylphenol to crystallization at a temperature in the range of about −25° to about 18° C. at which 2,6-diisopropylphenol crystallizes and the impurities do not, filtering and washing the 2,6-diisopropylphenol preferably with a non-polar aliphatic hydrocarbon. The solvent is removed from the product by distillation, and the product itself is recovered as a single fraction in the distillation. Such a procedure is not well suited for use in a large scale commercial operation.

U.S. Pat. No. 5,264,085 to M. Inaba, Y. Higaki, K. Jinno, M. Kataoka N. Sato and M. Honda describes a method of continuously separating components of a hydrous phenols mixture containing methanol by distillation. The method involves recovering methanol from the top of a single distillation column, dragging water containing phenols as a side stream from the recovery section of the distillation column and the dehydrated phenols as a bottom product.

THE INVENTION

This invention provides a new, economical and highly effective process for producing high purity 2,6-diisopropylphenol with the lower capital requirements of a batch distillation facility. More particularly, it has been found pursuant to this invention that washing impure 2,6-diisopropylphenol with aqueous alkali or alkaline earth metal hydroxide solution in an inert atmosphere prior to initiating distillation of the 2,6-diisopropylphenol completely eliminates the need for multi-column distillation procedures when seeking recovery of highly purified 2,6-diisopropylphenol.

The process described in detail herein will be in connection with purification of impure 2,6-diisopropylphenol, for which the process is particularly well adapted. Such impure 2,6-diisopropylphenol is typically a reaction product from the catalytic ortho-alkylation of phenol with propylene, and especially where the catalyst used is an aluminum phenoxide catalyst in accordance with an ortho-alkylation process like that described in the previously cited patent to Ecke and Kolka. Typically, such impure or crude 2,6-diisopropylphenol comprises from about 60 to about 80 wt % of 2,6-diisopropylphenol, from about 1 to about 4 wt % of phenol, from about 7 to about 21 wt % of ortho-isopropylphenol, from about 1 to about 8 wt % of 2,4,6-triisopropylphenol, and from 0 to about 4 wt % of one or more other phenolic compounds and/or phenolic ethers.

For convenience, 2,6-diisopropylphenol is hereinafter often referred to as "DIP". It will be understood that the term "inert environment" as used in the specification and claims hereof means that, to the extent reasonably practicable, the material is kept free from exposure to air, oxygen or other oxidizing materials that would result in the formation of impurities in the material when subjected to elevated temperatures.

In one of its embodiments, this invention provides a process for the purification of an impure DIP mixture which contains at least one phenolic component having a boiling point below that of DIP and at least one phenolic component having a boiling point higher than that of DIP. Such process comprises washing the impure DIP mixture with aqueous alkali metal or alkaline earth metal hydroxide solution in an inert atmosphere and separating the aqueous and organic phases, washing the resulting organic phase with water, and then subjecting the water-washed organic phase to distillation in an inert environment to produce purified 2,6-diisopropylphenol.

The phenolic components of the impure DIP mixture subjected to the process of this invention and having a boiling point below that of DIP may include, for example, phenol and/or one or more lower boiling mono-alkyl phenols. The higher boiling phenolic impurities include one or more triisopropyl phenols.

Any of the alkali or alkaline earth metal hydroxides may be used in the washing solution employed in the process of this invention. Typically, the alkali metal hydroxides will be sodium hydroxide or potassium hydroxide, or a combination of these, with sodium hydroxide being most preferred metal hydroxide for use in the practice of this invention. Calcium hydroxide is the preferred alkaline earth metal hydroxide. Mixtures of alkali metal hydroxide(s) and alkaline earth metal hydroxide(s) can also be used. In addition, alkali or alkaline earth metal oxide may be added to water to generate the alkali or alkaline earth metal hydroxide in situ. The aqueous alkali or alkaline earth metal solution will typically contain from about 1 wt % to about 50 wt % of the alkali metal hydroxide, and when using sodium hydroxide or potassium hydroxide, the solutions preferably will be about 10 to about 30 wt % solutions.

The impure DIP mixture may be washed one or more times with aqueous alkali metal hydroxide solution, followed by one or more water washes, all in an inert atmosphere. In a preferred embodiment, the impure DIP is washed at least twice with an alkali metal hydroxide or alkaline earth metal hydroxide solution prior to washing of the separated organic phase with water. The inert atmosphere may consist of any of the inert gases, including but not limited to nitrogen, helium, argon, or neon. Nitrogen is the preferred inert atmosphere for economic reasons. The use of an inert atmosphere limits exposure to air and creation of undesirable impurities which result from oxidation reactions when the DIP is exposed to temperatures such as during the ensuing distillation.

The order in which the impure DIP mixture and alkali or alkaline earth metal hydroxide solution are mixed to wash the impure DIP mixture is not crucial, permitting either the impure DIP mixture to be added to the metal hydroxide solution, or the metal hydroxide solution to be added to the impure DIP mixture, or the metal hydroxide solution and the impure DIP mixture to be added together simultaneously. After the impure DIP mixture has been washed with the aqueous alkali or alkaline earth metal hydroxide solution in an inert atmosphere, separation of the aqueous and organic phases may be achieved by decantation, centrifugation or other similar separation techniques, with decantation being the preferred method. The resulting aqueous phase will contain alkali or alkaline earth metal salts of the low boiling phenolic impurities such as phenol, one or more monoisopropyl phenols and less sterically hindered phenols such as 2,4-diisopropylphenol, and the like. Acidification of the aqueous waste solution enables recovery of these phenolic values, including small amounts of DIP extracted during the washing. Accordingly, the aqueous waste may be utilized as a source of phenolic materials (for example, as recycle in the catalyzed phenol ortho-alkylation process) upon acidification and recovery of the phenols from the washing solutions.

In a preferred embodiment, both the step of washing the impure DIP mixture with alkali metal hydroxide and/or alkaline earth metal hydroxide solution, and the washing of the resulting organic phase employ agitation of the materials. Various methods of agitation may be employed, including but not limited to shaking or stirring. In addition, during the washing with alkali and/or alkaline earth metal hydroxide solution and the washing with water, the temperature should be elevated to about 25° C. to about 100° C., preferably in the range of about 50° C. to about 100° C.

After the resulting organic phase is washed with water, the water-washed organic phase is distilled by any conventional means. Such distillation may be conducted on either a batch, semi-continuous or continuous basis, with batch distillation being the preferred method for economic reasons. The distillation should be conducted in an inert environment to reduce, if not eliminate, formation of impurities in the DIP through oxidation reactions at elevated temperatures.

The following examples serve to illustrate this invention, but do not limit it. In the examples all percentages are by weight unless otherwise indicated.

EXAMPLE 1

A caustic solution consisting of 73 grams of sodium hydroxide and 415 grams of water was slowly added to a stirred solution of 922.5 grams of crude DIP (68 wt % DIP; 16 wt % caustic) under a nitrogen pad. The mixture was heated to 65° C. and stirred for one hour at that temperature. The phases were then allowed to separate and the bottom caustic solution was collected into a beaker containing sufficient dilute sulfuric acid to neutralize all the caustic. To the remaining organic phase, 110 mL of 25 wt % caustic solution was added and the entire mixture was stirred at 50° C. for one hour. Again, the bottom caustic phase was separated and drained as before in the same dilute sulfuric acid solution. The remaining organic phase (total weight= 644 grams) was washed twice, each time with 300 mL of water at 50°–60° C. This sample was analyzed on a megapore 60 meter megabore column gas chromatograph under the following conditions:

| Temperature Program: | 150° C. | 200° C. | 265° C. |
|---|---|---|---|
| | 0 min. | 0 min. | 10 min. |
| | 3° C./min. | 15° C./min. | |
| Injector Temperature: | 300° C. | | |
| Carrier Gas: | He | | |
| Injecter Volume: | 0.1 microliter | | |
| Scan Range: | 35–300 amu | | |

The results obtained are listed below. The abbreviations used below and not previously defined have the following meanings: OIP=ortho-isopropylphenol; 2,4=2,4-diisopropylphenol; 2,5=2,5-diisopropylphenol, and 2,4,6=2,4,6-triisopropylphenol.

| | GC area % | | | | |
|---|---|---|---|---|---|
| | DIP | OIP | 2,4 | 2,5 | 2,4,6 |
| Crude DIP | | | | | |
| Before Wash | 68.2 | 17.3 | 0.85 | 2.66 | 6.4 |
| After Wash | 86 | 0.33 | 0.26 | 1.7 | 9.9 |

EXAMPLE 2

A crude 100 gram sample of DIP(68%) was stirred at 50° C. with aqueous caustic solution consisting of 7.94 grams of sodium hydroxide and 45 grams of water for 2 hours under a nitrogen pad. The phases were then allowed to separate and the bottom caustic solution was collected into a beaker containing 10.4 gms of phosphoric acid and 20 mL of water more than sufficient to neutralize all the caustic. To the remaining organic phase, 12 grams of 25 wt % caustic solution was added and the entire mixture was stirred at 50°–60° C. for one hour. Again, the bottom caustic phase was separated and drained as before in the same phosphoric acid solution. The remaining organic phase was washed several times with 60 mL of water each until the pH of the aqueous was between 7–8. Total weight of the organic phase was 70.3 grams. As in the previous example, the crude sample was analyzed by GC. The results obtained are listed below. The abbreviations used are the same as in the previous example.

|  | GC area % | | | | |
| --- | --- | --- | --- | --- | --- |
|  | DIP | OIP | 2,4 | 2,5 | 2,4,6 |
| Crude DIP |  |  |  |  |  |
| Before Wash | 68.21 | 17.3 | 0.85 | 2.66 | 6.4 |
| After Wash | 85.77 | 0.36 | 0.29 | 1.8 | 9.9 |

EXAMPLE 3

A crude 100 gram sample of DIP(68%) was stirred at 50°–60° C. with aqueous caustic solution consisting of 25 grams of sodium hydroxide and 125 grams of water for 1 hour under a nitrogen pad. The phases were then allowed to separate and the bottom caustic solution was drained off. To the remaining organic phase, 18.75 grams of NaOH in 55 grams water was added and the entire mixture was stirred at 50°–60° C. for one hour. Again, the bottom caustic phase was separated and drained off. The remaining organic phase was washed with 3×50 mL quantities of water until the pH of the aqueous was between 7–8. Total weight of the organic phase was 53 grams. As in the previous examples, the crude sample was analyzed by GC. The results obtained are listed below. The abbreviations used are the same as in the previous examples.

|  | GC area % | | | | |
| --- | --- | --- | --- | --- | --- |
|  | DIP | OIP | 2,4 | 2,5 | 2,4,6 |
| Crude DIP |  |  |  |  |  |
| Before Wash | 68.21 | 17.3 | 0.85 | 2.66 | 6.4 |
| After Wash | 85.4 | 0.19 | 0.18 | 1.2 | 11.05 |

EXAMPLE 4

The washed DIP mixtures produced as in Examples 1–3 above (total weight=746.8 grams) were combined and subjected to distillation conducted as described below.

Distillation of Table 1

Temperatures: Skin=290° C.; Pot=190°–210° C.; Overhead=180°–193° C. Vacuum=200 mm Hg; Reflux ratio=20:1 (fractions 1 & 2), 10:1 (all other fractions); Total distillation time=14 hours.

Results of this distillation are summarized in Table 1, wherein percentages are GC area percentages, except as otherwise specified. Abbreviations in Table 1 not previously defined have the following meanings: Cum.=cumulative; TIP=2,4,6-triisopropylphenol.

TABLE 1

| Cut | Wt., g | Wt. % | Cum. Wt % | OIP 18.4 | 18.8 | Olefin 19.0 | 20.4 | DIP 21.5 | 22.2 | 2,4 22.9 | 2,5 23.6 | TIP 24.1 |
| --- | --- | --- | --- | --- | --- | --- | --- | --- | --- | --- | --- | --- |
| Crude | 746.8 |  |  | 0.31 | 0.08 | 0.00 | 0.04 | 85.77 | 0.20 | 0.25 | 1.64 | 10.09 |
| 1 | 29.4 | 3.9 | 3.9 | 8.36 | 0.57 | 0.07 | 0.04 | 81.70 | 0.01 | 0.01 | 0.00 | 0.00 |
| 2 | 49.0 | 6.6 | 10.5 | 0.17 | 0.44 | 0.06 | 0.01 | 99.03 | 0.00 | 0.00 | 0.00 | 0.00 |
| 3 | 49.3 | 6.6 | 17.1 | 0.01 | 0.18 | 0.03 | 0.01 | 99.76 | 0.00 | 0.00 | 0.00 | 0.00 |
| 4 | 51.0 | 6.8 | 23.9 | 0.00 | 0.09 | 0.03 | 0.00 | 99.86 | 0.01 | 0.00 | 0.00 | 0.00 |
| 5 | 51.9 | 6.9 | 30.9 | 0.00 | 0.05 | 0.04 | 0.00 | 99.89 | 0.01 | 0.00 | 0.00 | 0.00 |
| 6 | 47.6 | 6.4 | 37.3 | 0.00 | 0.03 | 0.04 | 0.00 | 99.91 | 0.01 | 0.00 | 0.00 | 0.00 |
| 7 | 57.5 | 7.7 | 45.0 | 0.00 | 0.01 | 0.04 | 0.00 | 99.93 | 0.01 | 0.00 | 0.00 | 0.00 |
| 8 | 49.4 | 6.6 | 51.6 | 0.00 | 0.01 | 0.03 | 0.00 | 99.94 | 0.01 | 0.01 | 0.00 | 0.00 |
| 9 | 48.6 | 6.5 | 58.1 | 0.00 | 0.00 | 0.03 | 0.00 | 99.93 | 0.02 | 0.01 | 0.00 | 0.00 |
| 10 | 51.3 | 6.9 | 64.9 | 0.00 | 0.00 | 0.03 | 0.00 | 99.93 | 0.02 | 0.01 | 0.00 | 0.00 |
| 11 | 40.0 | 5.4 | 70.3 | 0.00 | 0.00 | 0.02 | 0.00 | 99.92 | 0.04 | 0.02 | 0.00 | 0.00 |
| Pot | 186.6 | 22.4 | 92.7 | 0.00 | 0.00 | 0.04 | 0.11 | 48.94 | 0.71 | 0.92 | 6.18 | 38.02 |

The column in Table 1 headed "Olefin" is of particular interest in that it represents an index of the extent to which the mixture undergoes undesirable oxidation reactions during the distillation. It can be seen that this impurity level was very small, especially in the cuts having very high DIP content.

In contrast, experiments in which known quantities of air were metered into a distilling mixture of crude DIP not subjected to the washing procedure of this invention, the impurity level was much higher. The starting material was crude DIP product formed by aluminum phenoxide catalyzed ortho-alkylation of phenol with propylene which had been subjected to a standard washing procedure to remove catalyst residues. The experiments were designed so as to allow a known quantity of air to be dialed into the system and to monitor the corresponding levels of impurities in various distillate fractions. The data indicates that there is a linear correlation between the amount of air and the impurity level. The results are presented in Tables 2 and 3 wherein percentages are GC area percentages, except as otherwise specified. A single impurity, 2-isopropenyl-6-isopropylphenol was used as the marker (i.e., as an indicator of impurity formation caused by oxidation under the distillation conditions). The conditions for the distillations when DIP was collected were as follows:

Distillation of Table 2

Temperatures: Skin=300° C.; Pot=198° C.; Overhead= 194° C. Vacuum=200 mm Hg; Reflux ratio=5:1; Total distillation time=8 hours Air flow=36 mL/min.

Distillation of Table 3

Temperatures: Skin=3100° C.; Pot=200° C.; Overhead= 193° C. Vacuum=200 mm Hg; Reflux ratio=5:1; Total distillation time=8 hours Air flow=16.4 mL/min.

Abbreviations used in Table 2 and Table 3 are the same as in Table 1.

TABLE 2

| Cut | Wt., g | Wt. % | Cum. Wt % | OIP 18.4 | Olefin 19.0 | 20.4 | DIP 21.5 | 22.2 | 2,4 22.9 | 2,5 23.6 | TIP 24.1 |
|---|---|---|---|---|---|---|---|---|---|---|---|
| Crude | 852.8 | | | 14.94 | 0.001 | 0.027 | 69.43 | 0.157 | 0.919 | 3.04 | 7.56 |
| Trap | 5.8 | 0.7 | 0.7 | | | | | | | | |
| 1 | 44.0 | 5.2 | 5.8 | 54.948 | — | — | 0.16 | — | — | — | — |
| 2 | 155.6 | 18.2 | 24.1 | 68.695 | 0.246 | 0.013 | 28.63 | 0.010 | 0.050 | 0.010 | — |
| 3 | 77.2 | 9.1 | 33.1 | 1.238 | 0.842 | 0.022 | 96.88 | 0.060 | 0.220 | 0.050 | 0.00 |
| 4 | 83.0 | 9.7 | 42.9 | 0.091 | 0.890 | 0.017 | 98.20 | 0.067 | 0.270 | 0.059 | 0.003 |
| 5 | 88.6 | 10.4 | 53.3 | 0.021 | 0.913 | 0.015 | 98.19 | 0.083 | 0.334 | 0.076 | 0.004 |
| 6 | 90.4 | 10.6 | 63.9 | 0.020 | 0.992 | 0.016 | 97.89 | 0.107 | 0.447 | 0.110 | 0.005 |
| 7 | 32.8 | 3.8 | 67.7 | 0.055 | 2.345 | 0.022 | 95.05 | 0.153 | 0.689 | 0.307 | 0.036 |
| 8 | 87.2 | 10.2 | 77.9 | 0.014 | 1.126 | 0.034 | 96.28 | 0.240 | 1.130 | 0.543 | 0.047 |
| 9 | 30.9 | 3.6 | 81.6 | 0.032 | 0.734 | 0.063 | 94.02 | 0.435 | 2.253 | 1.644 | 0.189 |
| 10 | 6.6 | 0.8 | 82.3 | 0.428 | 0.947 | 0.077 | 92.11 | 0.525 | 2.759 | 2.100 | 0.221 |
| Pot | 111.4 | 13.1 | 95.4 | 0.039 | 0.123 | 0.043 | 12.31 | 0.329 | 2.200 | 17.660 | 53.37 |

TABLE 3

| Cut | Wt., g | Wt. % | Cum. Wt % | OIP 18.4 | Olefin 19.0 | 20.4 | DIP 21.5 | 22.2 | 2,4 22.9 | 2,5 23.6 | TIP 24.1 |
|---|---|---|---|---|---|---|---|---|---|---|---|
| Trap | 6.6 | 0.6 | 0.6 | | | | | | | | |
| 1 | 59.6 | 5.2 | 5.8 | 48.564 | — | — | 0.10 | — | — | — | — |
| 2 | 126.3 | 11.1 | 16.9 | 90.000 | 0.028 | 0.008 | 6.63 | 0.00 | 0.01 | 0.00 | — |
| 3 | 91.1 | 8.0 | 24.9 | 15.847 | 0.398 | 0.053 | 80.95 | 0.03 | 0.09 | 0.02 | — |
| 4 | 97.5 | 8.6 | 33.4 | 1.253 | 0.491 | 0.036 | 97.23 | 0.048 | 0.138 | 0.02 | 0.001 |
| 5 | 86.5 | 7.6 | 41.0 | 0.153 | 0.483 | 0.029 | 98.61 | 0.058 | 0.170 | 0.028 | 0.002 |
| 6 | 75.3 | 6.6 | 47.6 | 0.028 | 0.485 | 0.025 | 98.81 | 0.066 | 0.196 | 0.032 | 0.002 |
| 7 | 178.2 | 15.6 | 63.3 | 0.013 | 0.483 | 0.025 | 98.77 | 0.091 | 0.269 | 0.047 | 0.003 |
| 8 | 88.0 | 7.7 | 71.0 | 0.009 | 0.520 | 0.030 | 98.11 | 0.129 | 0.406 | 0.081 | 0.004 |
| 9 | 81.0 | 7.1 | 78.1 | 0.012 | 0.536 | 0.051 | 97.70 | 0.193 | 1.040 | 0.145 | 0.010 |
| 10 | 50.6 | 4.4 | 82.5 | 0.017 | 0.500 | 0.150 | 96.18 | 0.398 | 1.439 | 0.552 | 0.038 |
| 11 | 29.3 | 2.6 | 85.1 | 0.025 | 0.382 | 0.229 | 90.53 | 0.888 | 3.696 | 3.265 | 0.370 |
| Pot | 150.9 | 13.2 | 98.3 | 0.003 | 0.025 | 0.059 | 5.29 | 0.262 | 1.442 | 14.877 | 53.079 |

The process of this invention is well suited for producing DIP in purities of 98.5% and above, and especially for product with purities of 99.8% or higher. In all such situations, only one distillation column would normally be required for producing products of such purity on a commercial scale. While this invention has been described in detail with reference to purification of DIP, the principles described herein may be applied, with appropriate modification of the operating conditions described herein, to the purification of other impure product mixtures having similar makeup and boiling characteristics.

It is to be clearly understood that recitations in this specification and/or in the claims hereof to the effect that the aqueous washing solution contains alkali and/or alkaline earth metal hydroxide or is an aqueous alkali metal hydroxide and/or aqueous alkaline earth metal hydroxide solution, etc., means that the solution is formed (a) by mixing at least one alkali metal hydroxide or alkaline earth metal hydroxide with water so that the alkali metal hydroxide or the alkaline earth metal hydroxide dissolves in the water and/or (b) by mixing at least one alkali metal oxide or alkaline earth metal oxide with water so that the alkali metal oxide or alkaline earth metal oxide goes into solution presumably through in situ chemical transformation to the hydroxide. In any such case, the mere fact that the alkali metal material in solution and/or the alkaline earth metal material in solution is probably, at least in part, in dissociated ionic form (e.g., as sodium cations and hydroxyl anions) is of no consequence. Thus, the claims are to be interpreted as covering the aqueous mixture formed by mixing alkali metal hydroxide and/or alkali metal oxide and/or alkaline earth metal hydroxide and/or alkaline earth metal oxide with water regardless of what inevitably takes place as a result of such mixing.

The entire disclosure of each and every U.S. patent referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the purification of an impure 2,6-diisopropylphenol mixture which contains at least one phenolic component having a boiling point below that of 2,6-diisopropylphenol and at least one phenolic component having a boiling point above that of 2,6-diisopropylphenol, said process comprising washing said mixture with aqueous alkali metal hydroxide solution and/or aqueous alkaline earth metal hydroxide solution in an inert atmosphere and separating the aqueous and organic phases, washing the resulting organic phase with water, and then subjecting the water-washed organic phase to distillation in an inert environment to recover purified 2,6-diisopropylphenol.

2. A process according to claim 1, wherein the metal hydroxide washing solution is aqueous alkali metal hydroxide solution.

3. A process according to claim 1, wherein the washing with aqueous metal hydroxide solution is conducted in at least two stages.

4. A process according to claim 1, wherein the washing with water is conducted in at least two stages.

5. A process according to claim 1, wherein the washing with aqueous metal hydroxide solution is conducted in at least two stages, and wherein the washing with water is conducted in at least two stages.

6. A process according to claim 1, wherein the washing with said aqueous metal hydroxide solution is conducted at an elevated temperature below the boiling point of said solution.

7. A process according to claim 1, wherein the metal of the metal hydroxide washing solution is sodium.

8. A process according to claim 1, wherein the washing with said aqueous metal hydroxide solution is conducted using a solution containing from about 15 to about 25 wt % of alkali metal hydroxide.

9. A process according to claim 8, wherein the alkali metal is sodium.

10. A process according to claim 1, wherein the washing is conducted with agitation.

11. A process according to claim 1, wherein in conducting said washing, the aqueous metal hydroxide solution is introduced into said impure 2,6-diisopropylphenol mixture.

12. A process according to claim 1, wherein said mixture comprises from about 60 to about 80 wt % of 2,6-diisopropylphenol, from about 1 to about 4 wt % of phenol, from about 7 to about 21 wt % of ortho-isopropylphenol, from about 1 to about 8 wt % of 2,4,6-triisopropylphenol, and from 0 to about 4 wt % of one or more other phenolic compounds and/or phenolic ethers.

13. A process according to claim 12, wherein the washing with aqueous metal hydroxide solution is conducted using aqueous alkali metal hydroxide.

14. A process according to claim 12, wherein the washing with aqueous metal hydroxide solution is conducted in at least two stages.

15. A process according to claim 12, wherein the washing with water is conducted in at least two stages.

16. A process according to claim 12, wherein the washing with aqueous metal hydroxide solution is conducted in at least two stages, and wherein the washing with water is conducted in at least two stages.

17. A process according to claim 12, wherein the washing with aqueous metal hydroxide solution is conducted at an elevated temperature below the boiling point of said solution.

18. A process according to claim 12, wherein the metal of the metal hydroxide washing solution is sodium.

19. A process according to claim 12, wherein the washing with metal hydroxide solution is conducted using a solution containing from about 15 to about 25 wt % of alkali metal hydroxide.

20. A process according to claim 19, wherein the alkali metal is sodium.

21. A process according to claim 12, wherein the washing is conducted with agitation.

22. A process according to claim 12, wherein in conducting said washing, the aqueous metal hydroxide solution is introduced into said impure 2,6-diisopropylphenol mixture.

23. A process according to claim 12, wherein said distillation is a batch distillation conducted under an inert environment.

24. A process according to claim 12, wherein said distillation is a continuous distillation conducted under an inert environment.

25. A process according to claim 12, wherein:

a) the washing with aqueous metal hydroxide solution is conducted in at least two stages with agitation and at an elevated temperature below the boiling point of said solution;

b) the washing with water is conducted with agitation in at least two stages; and c) said distillation is conducted under an inert environment.

26. A process according to claim 25, wherein the metal of the metal hydroxide washing solution is sodium, potassium or calcium or a mixture of at least two of these metals.

27. A process according to claim 26, wherein the solution contains from about 15 to about 25 wt % of said metal hydroxide, and wherein in conducting said washing, the solution is introduced into said impure 2,6-diisopropylphenol mixture.

* * * * *